United States Patent [19]

Stiefel

[11] 4,036,991
[45] July 19, 1977

[54] SKIN TREATMENT WITH EMOLLIENT CIS-6-HEXADECENOIC ACID OR DERIVATIVES

[75] Inventor: Werner K. Stiefel, Oak Hill, N.Y.

[73] Assignee: Stiefel Laboratories, Inc., Oak Hill, N.Y.

[21] Appl. No.: 220,369

[22] Filed: Jan. 24, 1972

[51] Int. Cl.$^2$ .............. A61K 7/00; A61K 7/40; A61K 9/06; A61K 31/19
[52] U.S. Cl. .................. 424/365; 424/47; 424/69; 424/95; 424/195; 424/305; 424/312
[58] Field of Search .......... 424/95, 195, 305, 312, 424/365, 47, 69

[56] References Cited

U.S. PATENT DOCUMENTS

| 2,954,325 | 9/1960 | Baumann | 424/365 |
| 3,660,566 | 5/1972 | Vinson | 424/47 |

OTHER PUBLICATIONS

Shinohara, Chem. Abs., vol. 74, 1971, p. 157, No. 40070g.
Jacobs, Chem. Abs., vol. 67, 1967, p. 4839, No. 51709d.
Czetsch-Lindenwald, Salben-Puder-Externa Springer--Verlag, Berlin, 1950, pp. 12–21.
Spencer, Chem. Abs., vol. 76, 1972, No. 23029.
Cross, Chem. Abs., vol. 52, 1958, p. 757.
Barnett, D & C Ind., Mar. 1960, vol. 86, pp. 330, 331.
Sagarin, Cos. Sci. & Tech., Interscience Pub., NY, 1957, pp. 106–109, 118.

Primary Examiner—Albert T. Meyers
Assistant Examiner—A. P. Fagelson
Attorney, Agent, or Firm—Pennie & Edmonds

[57] ABSTRACT

A composition that may be used as the base vehicle for cosmetic or therapeutic preparations that are applied to the human skin contains as one of the essential constituents thereof at least one member of the group consisting of cis-6-hexadecenoic acid and the glycerol, glycol and monohydric alcohol esters of cis-6-hexadecenoic acid.

4 Claims, No Drawings

SKIN TREATMENT WITH EMOLLIENT CIS-6-HEXADECENOIC ACID OR DERIVATIVES

BACKGROUND OF INVENTION

1. Field of Invention

This invention relates to compositions for topical application to the human skin.

2. Prior Art

The human skin serves a variety of functions which include the protection of the body from the external environment. The skin accomplishes this task in various ways one of which is the production of skin lipids the main source of which is the sebum exuded by the sebaceous glands of the skin. The sebaceous gland exudate, upon spreading over the skin, tends to thicken and form a protective layer that is lubricious and emollient, thus contributing to the suppleness of the skin as well as conserving skin moisture and providing an inhospitable environment for the survival of pathogenic microorganisms of the skin. Sebum, the skin's endogenous lubricant, consists of about one-third cis-6-hexadecenoic acid and its triglyceride and wax esters. Man is the only animal whose skin is known to manufacture this lipid substance, and until recently it was not known to exist in nature anywhere except as a constituent of human sebum.

In order to supplement or supplant the lubricious and protective properties of human sebum for cosmetic or therapeutic purposes it is common to apply oily or creamy emollient compositions to the skin. These emollient compositions contain lipid substances and may be in the form of creamy aqueous emulsions or in the form of creamy blends or emulsions of nonaqueous (eg., organic) substances. In addition to the lipid constituent or constituents (and, in the case of aqueous creams and lotions, water and oil emusifier) these compositions may contain an almost infinite variety of other ingredients such as perfumes, colors, preservatives, stabilizers, thickeners, moisturizing agents and medicinal substances, depending upon the intended use of the composition (eg., cosmetic or therapeutic). In all cases, these compositions contain as the principal lipid constituent thereof one or more oils or fats derived from animal, vegetable or mineral sources. However, to date, all of these oils and fats are largely composed of substances not normally found on the human skin surface. They may perform their emollient and protective functions well enough, but they are nonetheless foreign substances as far as the skin's normal biochemistry is concerned and may occasionally be the cause of allergic reactions and similar disturbances of the skin. Moreover, many lipids of animal and vegetable origin provide a fertile growth medium for mold and pathogens necessitating the use of preservatives in the composition which may also irritate the skin.

It has recently been found that the oil of the seed of certain plants, and in particular plants belonging to the Thunbergia genus, is composed predominantly of the triglyceride and wax esters of cis-6-hexadecenoic acid. After an intensive investigation I have discovered that this oil, and highly purified cis-6-hexadecenate fractions thereof, can be combined with water and other fluid vehicles to form aqueous and non-aqueous creams and ointments that have outstanding emollient and protective properties when applied to the skin. Furthermore, since the lipid constituent of my new emollient comprises a fat natural to the human skin, the small but significant number of allergic reactions encountered with the foreign oils and fats currently employed as emollients is largely eliminated.

SUMMARY OF THE INVENTION

Pursuant to my aforesaid discovery I have now developed a new and improved emollient composition that may be used as such or as the base for more elaborate cosmetic or therapeutic preparations. Accordingly, the improved cosmetic and therapeutic base composition of the invention contains, as one of the essential constituents thereof, at least one member of the group consisting of cis-6-hexadecenoic acid, the mono-, di- or triglycerides of cis-6-hexadecenoic acid, mixed glycerides containing cis-6-hexadecenoic as at least one of the fatty chains, the mono- and di-cis-6-hexadecenoic acid esters of ethylene and propylene glycols, and the cis-6-hexadecenoic acid esters of straight chain and branched (iso-) monohydric alcohols. The composition additionally contains aqueous or non-aqueous fluid or solid constituents with which the aforesaid lipid substance is blended or emulsified, and it may contain emulsifiers, other lipids or emollients, extenders, colors, perfumes and/or medicinal agents, depending on the intended use of the composition as a cosmetic or therapeutic preparation.

DETAILED DESCRIPTION

Sebum, the endogenous lubricant exuded by the sebaceous glands of the human skin, is a unique substance the properties and composition of which have been intensively investigated. As a result, sebum has been found to comprise about one third cis-6-hexadeceonic acid and the triglycerides and wax esters of this fatty acid. In addition to its lubricious and emollient properties, sebrum has been found to provide an inhospitable substrate for the survival, or at least the growth, of pathogenic microorganisms. Moreover, extensive research and investigation have failed to disclose the presence of cis-6-hexadecenoic acid or its derivatives in the skin exudate of any animal other than man, and it may be inferred that it is the presence of this unique fatty acid in human sebum that imparts to sebum many, if not most, of its unique properties.

Cis-6-hexadecenoic acid is a monoene fatty acid the formula for which may be written as follows:

$$CH_3(CH_2)_8CH{:}CH(CH_2)_4COOH$$

As noted, man is the only animal whose skin is known to manufacture this fatty acid and its derivatives, and until recently it was not known to exist in any other oil or fat of natural origin. Recent investigations by researchers in the botanical and agricultural fields have disclosed the presence of this fatty acid as a minor constituent of *Picramnia sellowii* and *Beauprea balansae* seed oils and as a major constituent of *Thunbergia alata* seed oil. By way of example, the seed oil of *Thunbergia alata* is recovered from the seed of this plant by grinding the seed and then extracting the seed oil with a volatile solvent or by a steam process. In the present case, the oil was extracted by the use of petroleum ether and a soxhlet extraction apparatus. The solvent was evaporated to near dryness and then removed completely by a flow of nitrogen. The resulting seed oil contains about 85% by weight cis-6-hexadecenoic acid and its derivatives, and has the following properties.

TABLE I

| | |
|---|---|
| HBr equivalent, %* | 0.7 |
| Refractive index, $n_D40$ | 1.4625 |
| Iodine value, by analysis | 88.7 |
| Iodine value, calculated | 88.8 |

*As epoxyoleic acid

The seed oil contains minor amounts of other lipid constituents (for example, cis-7-hexadecenoic acid, cis-8-octadecenoic acid, cis-9-octadecenoic acid, palmitic acid, linoleic acid, and their derivitives) which are themselves oily or emollient substances and which do not impair the effectiveness of the preponderant cis-6-hexadecenoic constituent of the oil. Therefore, although the seed oil can be further refined by conventional techniques to obtain substantially pure cis-6-hexadecenoic acid (and its derivitives) for use in the practice of my invention, the pure seed oil as extracted from the plant seed can equally well be used as the essential lipid ingredient in most formulations of the composition of the invention.

The cis-6-hexadecenoic acid is present in the oil predominantly in the form of the triglyceride of this fatty acid. However, I found that other oily or waxy derivitives of cis-6-hexadecenoic acid, as well as the uncombined acid itself, can equally well be employed as the essential lipid ingredient of my new skin composition. Thus, the oily or waxy derivitives of cis-6-hexadecenoic acid useful in the practice of the invention include, but are not limited to, the mono-, di-and triglycerides of cis-6-hexadecenoic acid, the mixed glycerides containing cis-6-hexadecenoic as at least one of the fatty chains, the cis-6-hexadecenoic acid esters of straight chain and branched (iso-) alcohols of from one to twenty or more carbon atoms, and the mono- and di-cis-6-hexadecenoic acid esters of ethylene and propylene glycol.

As previously noted, cis-6-hexadecenoic acid and its oily or fatty derivitives comprise the essential lipid constituent of the skin treatment composition of the invention. The essential cis-6-hexadecenoic lipid ingredient of the composition may be mixed with water and a conventional emulsifier to form aqueous creams and lotions or with organic or mineral vehicles to form non-aqueous ointments, oils and creams and the like. These creamy or oily compositions may then be used on the skin without further additions thereto, or they may be used as the base for more specialized cosmetic or therapeutic preparations. Thus, the composition may also include other lipid substances which enhance or modify the emollient properties of the base composition, as well as emulsifiers, stabilizers, thickeners, extenders and medicinal agents of known utility, and colors and perfumes for esthetic purposes.

Lipid substances that may be used to enhance or modify the emollient properties of my new skin composition include, but are not limited to, oils of natural origin such as almond oil, coconut oil, olive oil, palm oil, peanut oil and the like, fatty acids such as lauric acid, myristic acid, palmitic acid, stearic acid and the like, the unsaturated homologues of these fatty acids, the monohydric alcohol esters of the fatty acids such as ethyl laurate, iso-propyl laurate, ethyl myristate, n-propyl myristate, isopropyl myristate, ethyl palmitate, isopropyl palmitate, methyl palmitate, methyl stearate, ethyl stearate, isopropyl stearate, butyl stearate, isobutyl stearate, amyl stearate, isoamyl stearate and the like, the mono- and di-glycol esters of the fatty acids, and the mono-, di-, tri- and mixed glycerol esters of the fatty acids. Non-lipid substances that may be employed to modify the emollient properties of the composition include, but are not limited to, the straight chain and branched aliphatic alcohols such as ethanol, propanol, isopropanol, hexanol, octanol, lauryl alcohol, myristyl alcohol, stearyl alcohol and the like, and the glycols such as ethylene glycol, diethylene glycocol, polyethylene glycol, propylene glycol and the like. The aforementioned substances for modifying the emollient properties of the composition are merely representative, and are not limitative, of those substances which are known in the cosmetic and pharmaceutical arts to be generally useful for this purpose.

As noted, emulsifiers, stabilizers, thickeners and extenders of known utility in the cosmetic and pharmaceutical arts may also be included in the composition of the invention to modify its appearance and physical properties. The selection of a particular emulsifier or stabilizer or thickener or extender from among all of those of known utility in these arts is a matter within the skill of an experienced formulator of cosmetic and pharmaceutical preparations. Examples of such formulations prepared in accordance with the practice of the present invention are set forth in the following specifice examples.

EXAMPLE I

| Ingredient | % By Wt. |
|---|---|
| Cis-6-hexadecenoic triglyceride | 50.00 |
| Stearic acid, triple pressed | 0.54 |
| Sodium borate (borax) | 0.35 |
| Demineralized water | 49.11 |

The borax was dissolved in water at 75° C., and the cis-6-hexadecenoic triglyceride and the stearic acid were mixed together and heated to 75° C. with stirring. The hot borax solution was then added to the hot lipid mixture with stirring, and the resulting emulsion was then cooled to room temperature with continued stirring. The product is a white cream of particular utility in the care of dry skin.

EXAMPLE II

| Ingredient | % By Wt. |
|---|---|
| Cis-6-hexadecenoic triglyceride | 50.00 |
| Stearic acid, triple pressed | 0.54 |
| Sodium borate (borax) | 0.35 |
| Aldo 158* | 5.0 |
| Demineralized water | 44.11 |

*A $C_{14} - C_{18}$ straight chain fatty vicinal glycol; Ashland Chemical Co.

This composition was prepared in the same manner as the composition of Example I, the Aldo 158 being added thereto as a stabilizer for the composition. The product is a white cream for dry skin care.

EXAMPLE III

| Ingredient | % By Wt. |
|---|---|
| Cis-6-hexadecenoic triglyceride | 40.0 |
| Polyoxyethylene 40 stearate | 8.0 |
| Stearyl alcohol | 20.0 |
| Propylene glycol | 12.0 |
| Demineralized water | 20.0 |

The stearyl alcohol, cis-6-hexadecenoic triglyceride, polyoxyethylene 40 stearate and propylene glycol were mixed and heated to 70° C. To the hot mixture, hot water (70° C.) was added during stirring. After the addition of water, the emulsified mixture was cooled with continued stirring until mixture reached 25° C. The product is a white cream for dry skin care.

EXAMPLE IV

| Ingredient | % By Wt. |
|---|---|
| Cis-6-hexadecenoic triglyceride | 20.0 |
| Arlacel 186* | 3.0 |
| Polyoxyethylene 20 sorbitan monooleate | 1.0 |
| Magnesium aluminum silicate | 3.0 |
| Sodium carboxymethylcellulose | 0.5 |
| Glycerol | 12.0 |
| Beeswax | 0.4 |
| Demineralized wager | 60.1 |

*Mixture of mono- and diglycerides of fatty acids; Atlas Chemical Industries, Inc.

The magnesium aluminum silicate and the sodium carboxymethylcellulose were added to water at 70° C. during stirring, and the hot dispersion was stirred for an additional 20 minutes. To this hot dispersion was added a heated mixture (70° C.) of Arlacel 186 and glycerol. A hot mixture (70° C.) of beeswax, cis-6-hexadecenoic triglyceride and polyoxyethylene 20 sorbitan monooleate was then added with stirring, and the resulting emulsion was cooled to room temperature with stirring. The product is a white lotion for general skin care.

EXAMPLE V

| Ingredient | % By Wt. |
|---|---|
| Cis-6-hexadecenoic triglyceride | 80.0 |
| Beeswax | 10.0 |
| Sorbitan sesquioleate | 10.0 |

A mixture of beeswax, sorbitan sesquioleate and cis-6-hexadecenoic triglyceride was heated at 70° C. with stirring. After the beeswax had completely melted, the mixture was cooled to room temperature with continued stirring. The product is a non-aqueous lotion for dry skin care.

EXAMPLE VI

| Ingredient | % By Wt. |
|---|---|
| Cis-6-hexadecenoic triglyceride | 25.0 |
| Stearyl alcohol | 25.0 |
| Propylene glycol | 12.0 |
| Polyoxyethylene 40 stearate | 5.0 |
| Demineralized water | 33.0 |

The stearyl alcohol, propylene glycol, polyoxyethylene 40 stearate and cis-6-hexadecenoic triglyceride were mixed and heated to 70° C. with stirring. Hot water (at 70° C.) was then added to the hot lipid mixture with stirring. The resulting emulsion was then cooled to room temperature with continued stirring. This product has a cream consistency and is used for general skin care (for example, as a night cream).

EXAMPLE VII

| Ingredient | % By Wt. |
|---|---|
| Cis-6-hexadecenoic triglyceride | 3.5 |
| Cis-6-hexadecenoic acid | 3.0 |
| Cetyl alcohol | 0.5 |
| Glycerol | 2.0 |
| Sodium lauryl sulfate powder | 0.1 |
| Triethanolamine | 0.5 |
| Demineralized water | 90.4 |

The sodium lauryl sulfate powder was dissolved in a solution containing glycerol and triethanolamine, and the solution was heated to 70° C. A heated mixture (70° C.) of cis-6-hexadecenoic triglyceride, cetyl alcohol and cis-6-hexadecenoic acid was then added to the aqueous solution with stirring. The resulting emulsion was then cooled to room temperature during continued stirring. This product is a white opaque lotion for general skin care (for example, as a day cream).

EXAMPLE VIII

| Ingredient | % By Wt. |
|---|---|
| Cis-6-hexadecenoic triglyceride | 4.50 |
| Stearic-acid, triple pressed | 4.00 |
| Polyoxyethylene 20 sorbitan monolaurage | 0.15 |
| Carboxyl vinyl polymer* | 0.30 |
| Triethanolamine | 0.40 |
| Demineralized water | 90.65 |

*Carbopol 940; B. F. Goodrich Co.

The carboxyl vinyl polymer was added with vigorous stirring to approximately one-half of water available in the formula, and the dispersion was heated with continued stirring at 50° C. until the Carbopol 940 had dissolved. Then the polyoxyethylene 20 sorbitan monolaurate, the rest of water and the triethanolamine were added to the hot solution with continued stirring, while raising the temperature of this solution to 70° C. Then a mixture of stearic acid and cis-6-hexadecenoic triglyceride previously heated to 70° C. was added to the hot aqueous solution with stirring, and the resulting emulsion was cooled to room temperature. This product is a white cream for normal skin care.

EXAMPLE IX

| Ingredient | % By Wt. |
|---|---|
| Cis-6-hexadecenoic acid | 5.0 |
| Magnesium stearate | 5.0 |
| Zinc stearate | 5.0 |
| Talc, cosmetic grade | 85.0 |

The cis-6-hexadecenoic acid, zinc stearate and magnesium stearate were mixed with an equal portion of talc. This mixture was then added to the remaining talc, and then was blended and screened to obtain a fine powder product. The product has antifungal properties and is particularly useful as a foot powder.

EXAMPLE X

| Ingredient | % By Wt. |
|---|---|
| Cis-6-hexadecenoic triglyceride | 95.5 |
| Polyoxyethylene polyol fatty acid ester | 1.5 |
| Polyoxyethylene 2 oleyl ether | 3.0 |

The polyoxyethylene polyol fatty acid ester and the polyoxyethylene 2 oleyl ether were added to the cis-6-hexadecenoic triglyceride at room temperature with continued stirring until the solution is clear. This product is a dispersible oil for use as an additive to bath water.

EXAMPLE XI

| Ingredient | % By Wt. |
|---|---|
| Cis-6-hexadecenoic triglyceride | 15.0 |
| Polyoxyethylene 4 lauryl ether | 5.0 |

EXAMPLE XI-continued

| Ingredient | % By Wt. |
| --- | --- |
| Ethyl alcohol, anhydrous | 50.0 |
| Freon 12/114 (60:40) | 30.0 |

This formula describes the composition of an aerosol bath oil spray for use after bathing or showering.

The foregoing specific examples are representative, but are not limitative, of my new composition. These and other such compositions of the invention may be applied to the skin without modification, or they may be employed as the base vehicle to which other ingredients (eg., colors or perfumes or medicinal agents or the like) are added for application to the skin. As previously noted, the essential lipid constituents of my new composition is cis-6-hexadecenoic acid and its derivitives and, as exemplified by the aforesaid specific examples, this lipid constituent may comprise from about 3% to about 95% by weight of the composition. As cis-6-hexadecenoic acid and its derivitives are one of the principal lipid constituents of the sebaceous exudate of the human skin, the composition of the invention has outstanding emollient and protective properties when applied to the skin. Moreover, as previously noted, as the essential lipid constituent of the composition is a lipid uniquely natural to the human skin, the small but significant number of allergic reactions encountered with the foreign oils and fats currently employed as emollients is largely eliminated.

I claim:

1. A method of benefically treating human skin which comprises applying to the skin a composition comprising an admixture of an emollient base with a cosmetic or therapeutic constituent, said base having as its essential emollient constituent at least one lipid substance selected from the group consisting of cis-6-hexadecenoic acid, the mono-, di- and triglycerides of cis-6-hexadecenoic acid, mixed glycerides containing cis-6-hexadecenoic as at least one of the fatty chains, the mono- and di- cis-6-hexadecenoic acid esters of ethylene and propylene glycols, and the cis-6-hexadecenoic acid esters of straight chain and branched chain monohydric alcohols, said lipid constituent comprising from about 3% to about 95% by weight of said composition.

2. The method according to claim 1 in which the composition is an emulsion composed essentially of said essential lipid constituent, a non-aqueous fliud and an emulsifier therefor.

3. The method according to claim 1 in which the composition is an emulsion composed essentially of said essential lipid constituent, water, and an emulsifier therefor.

4. The method according to claim 3 in which said essential lipid constituent comprises from about 3% to about 80% of said emulsion.

* * * * *